United States Patent [19]

Buyalos et al.

[11] Patent Number: 5,236,558

[45] Date of Patent: Aug. 17, 1993

[54] METHOD TO RECYCLE SPENT ETHYLENE GLYCOL

[75] Inventors: Edward J. Buyalos, Chester; David Pendlebury, Chesterfield; Lon K. Bouknight, Richmond, all of Va.; Neil F. Blake, Wake; Clarence McKeithan, Jr., Sanford Lee, both of N.C.

[73] Assignee: Allied-Signal Inc., Morris Township, Morris County, N.J.

[21] Appl. No.: 588,635

[22] Filed: Sep. 26, 1990

Related U.S. Application Data

[63] Continuation-in-part of Ser. No. 6,333, Feb. 2, 1987, abandoned, which is a continuation of Ser. No. 422,328, Sep. 23, 1982, abandoned.

[51] Int. Cl.$^5$ ............................................. B01D 3/10
[52] U.S. Cl. ............................. 203/18; 203/20; 203/25; 203/93; 203/94; 203/97; 203/98; 203/DIG. 8; 528/308.7; 528/496; 568/871
[58] Field of Search .................. 203/92, 96, 20, 97, 203/18, 25, 93, 94, 98, DIG. 8; 528/272, 496, 308.7; 568/871; 202/205, 264; 526/65

[56] References Cited

U.S. PATENT DOCUMENTS

| | | | |
|---|---|---|---|
| 3,109,831 | 11/1963 | Seiner | 526/65 |
| 3,109,832 | 11/1963 | Seiner | 526/68 |
| 3,109,833 | 11/1963 | Seiner | 526/68 |
| 3,109,834 | 11/1963 | Seiner | 526/68 |
| 3,367,847 | 2/1968 | Pierson | 203/41 |
| 3,408,268 | 10/1968 | Pitts et al. | 203/78 |
| 3,590,072 | 6/1971 | Seybourne | 560/94 |
| 4,110,316 | 8/1978 | Edging et al. | 526/68 |
| 4,146,729 | 3/1979 | Goodley et al. | 560/94 |

Primary Examiner—Virginia Manoharan

[57] ABSTRACT

A method to recycle spent ethylene glycol in a continuous process for the manufacture of polyethylene terephthalate in at least one reactor vessel which includes:
a. condensing the overhead vapor of spent ethylene glycol, water and other byproducts from the reactor vessel,
b. feeding the condensed vapor to a single distillation column,
c. removing only part of the water and other byproducts from ethylene glycol by distillation overhead in the column and
d. feeding the resultant bottoms of the column back to the reactor vessel as recycle ethylene glycol along with virgin ethylene glycol, so that polyethylene terephthalate polymer being manufactured by the continuous process is essentially unaffected regarding polymer color and ability to be spun into high quality yarn, but with lower diethylene glycol content that polymer made from all virgin ethylene glycol.

11 Claims, 1 Drawing Sheet

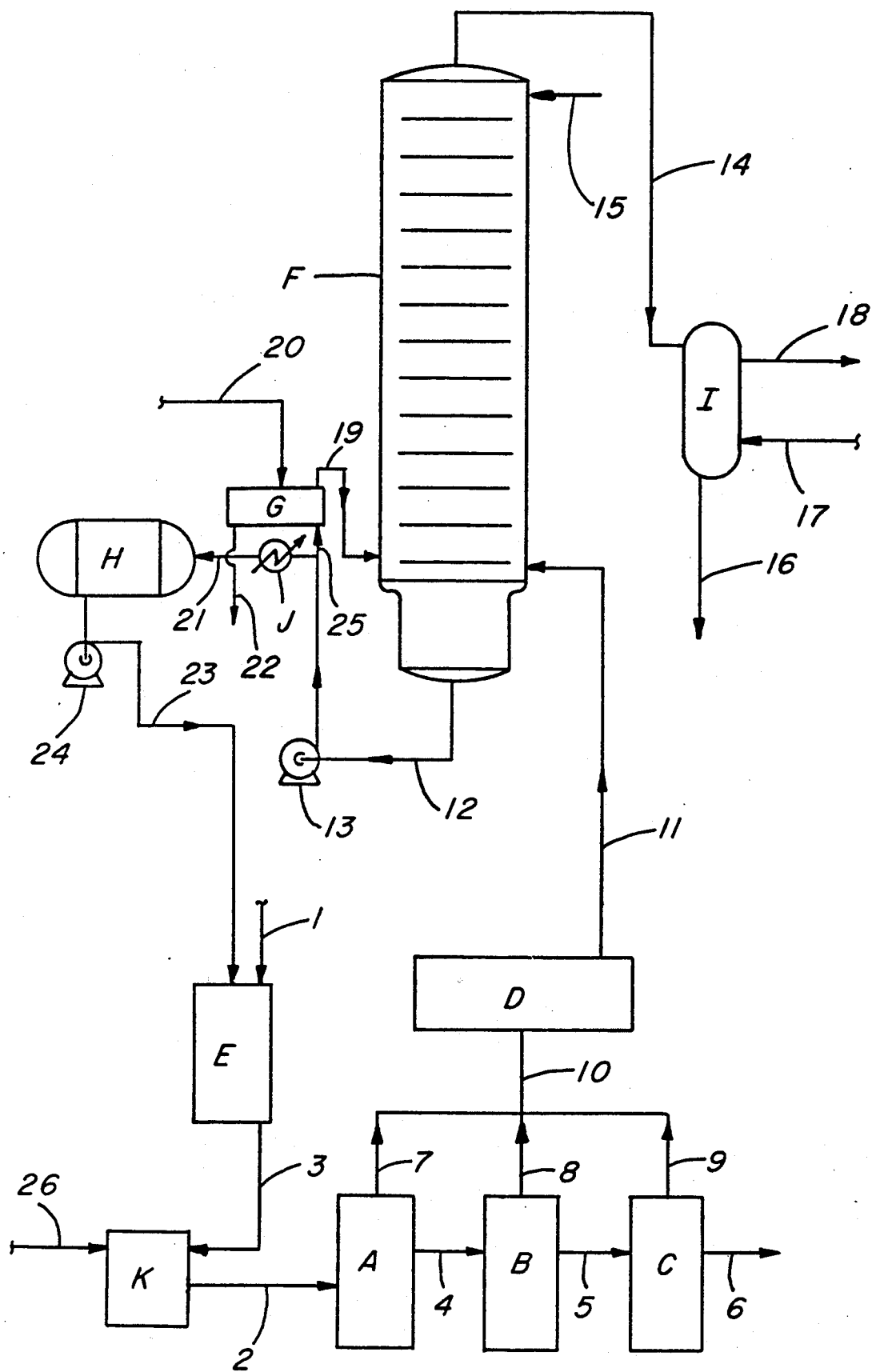
FIG. I

METHOD TO RECYCLE SPENT ETHYLENE GLYCOL

This application is a continuation in part of U.S. Ser. No. 006,333 filed Feb. 2, 1987, now abandoned which in turn is a continuation of U.S. Ser. No. 422,328, filed Sep. 23, 1982.

BACKGROUND OF THE INVENTION

This invention relates to a method to recycle spent ethylene glycol during the esterification of polyethylene terephthalate.

Prior art methods to recover and/or recycle spent ethylene glycol from a method to manufacture polyesters are described in U.S. Pat. Nos. 4,146,729, 4,110,316, 3,590,072, 3,367,847, 3,408,268, 3,109,831, 3,109,832, 3,109,833 and U.S. Pat. No. 3,109,834, all hereby incorporated by reference, in toto. Also see Great Britain 1 077 379.

SUMMARY OF THE INVENTION

None of the prior art methods feed concentrated ethylene glycol to a single distillation column to remove only a portion of the water and other byproducts before recycling the recovered spent ethylene glycol. Applicants have surprisingly found that, in spite of leaving water and other byproducts in the recovered, recycled spent ethylene glycol, when blended with virgin ethylene glycol and reacted with terephthalic acid (as described in prior art U.S. Pat. No. 3,689,461, hereby incorporated by reference in toto) that polymer quality is unaffected regarding color and ability to be spun into high quality tire and industrial yarn. Also most surprising is the fact that the diethylene glycol content of the polymer prepared is lower than that prepared from all virgin ethylene glycol. This invention is a method to recycle spent ethylene glycol in a continuous process for the manufacture of polyethylene terephthalate in at least one reactor vessel comprising:

a. condensing the overhead vapor of spent ethylene glycol, water and other byproducts from the reactor vessel, b. feeding the condensed vapor to a single distillation column, c. removing only part of the water and other byproducts from ethylene glycol by distillation overhead in the column and d. feeding the resultant bottoms of the column back to the reactor vessel as recycle ethylene glycol along with virgin ethylene glycol, with the recycle ethylene glycol containing at least about 1 but less than about 3 percent by weight of solids, so that polyethylene terephthalate polymer being manufactured by the continuous process is substantially unaffected regarding polymer color and ability to be spun into high quality yarn but with lower diethylene glycol content than polymer color and ability to be spun into high quality yarn but with lower diethylene glycol content than polymer from all virgin ethylene glycol. It is preferred that the feed to the column contain from about 45 to about 55 percent ethylene glycol and the overhead from the distillation column contains from about 1/10 to 1 percent ethylene glycol while the bottom of the distillation column which is to be recycled contains at least about 1.2 but less than about 2.5 percent by weight of solids and from about 85 to 95 percent ethylene glycol. It is also preferred to reflux the column with 100 percent clarified water at a reflux ratio from about 0.12 to 1. The preferred temperature at the bottom of the distillation column is between about 130° C. and 150° C., while the temperature at the top of the distillation column is from about 100° C. to 105° C. when operating at atmospheric pressure. The preferred pressure on the column is between 400 Torr and 800 Torr, adjusting the top and bottoms column temperatures to correspond, so that the overhead still contains only 1/10 to 1 percent ethylene glycol. The preferred distillation column has from about 10 to about 16 distillation plates. The preferred feed rate to the distillation column is from about 8 to about 12 gallons (30 to about 45 liters) per minute at a temperature of about 65° C. and is fed to the third distillation plate in the column. It is also preferred to recirculate the bottoms from the distillation column through a reboiler for heating to achieve the preferred bottom temperature of between about 130° and 150° C. The preferred rate of recirculation through the reboiler is between about 850 and 1250 gallons (3200 and 4730 liters) per minute and steam is preferred to be fed to the boiler at about 3500 to 4500 pounds (1590 to 2045 kilograms) per hour at a pressure of between 110 and 140 psig (7.7 and 10.2 kg/cm$^2$). It is highly preferred to use an antifoaming compound added to the recycle system, either most preferably to the recycle ethylene glycol after cooling or in the distillation column or anywhere else in the system. The preferred method of this invention takes place in a multiple reactor vessel polyethylene terephthalate esterification system.

BRIEF DESCRIPTION OF THE DRAWING

The FIGURE is a schematic showing the apparatus used to carry out the method of this invention.

DETAILED DESCRIPTION

The vessels involved are a first reactor A, second reactor B, third reactor C, a condenser D, an ethylene glycol feed tank E, a distillation column F, a reboiler G for the distillation column, recycle ethylene glycol storage tank H, a condenser I for the distillation column F, a cooler J for the recycle of ethylene glycol and paste mixer K. Virgin ethylene glycol is fed to ethylene glycol feed tank E through feed line 1 and mixed with recycled ethylene glycol being fed through recycle ethylene glycol feed line 23. The mixed ethylene glycol from tank E is fed through line 3 to past mixer K along with terephthalic acid fed through line 26. Ethylene glycol and terephthalic acid are then fed to first reactor A through line 2. Esterification occurs according to the prior art in series to first reactor A, second reactor B and third reactor C through the transfer lines 4, 5 and 6 while the overhead vapors pass through lines 7, 8 and 9 to be collected in line 10 and condensed in condenser D then the liquid condensed vapors are fed through line 11 to column F. Any pumps necessary on lines 1 through 11 are omitted as being an obvious expedient to one skilled in the art. In column F the bottom of the column F is pumped by pump 13 through line 12 to reboiler G and back into distillation column F through line 19. Steam is fed to reboiler G through line 20 and steam condensate is exhausted to line 22. Line 12 feeds line 25 to reboiler G and also to cooler J on line 21 to recovered ethylene glycol storage tank H which has pump 24 to pump the recovered ethylene glycol and recycle it through line 23 to ethylene glycol feed tank E. Water, other byproducts and a small portion of ethylene glycol in the overhead from column F through line 14 are condensed in condenser I and discarded to line 16 for disposal. Condenser I is fed by water to condenser spray through line 17 from a cooling tower not shown and the water is recirculated to the cooling tower through line 18. Also clarified or clean soft tap water is refluxed through line 15 to column F.

EXAMPLE

Using the apparatus shown in the Figure and described above, soft pure clarified tap water is fed to reflux line 15 at a rate of one gallon (3.8 liters) per minute. The feed to column F through line 11 from condenser D consists of about 47 to 53 percent ethylene glycol and the rest water and other byproducts, predominantly water. The overhead from column F is about 0.5 percent ethylene glycol, over 99 percent water and a small fraction of a percent of byproducts from the polyethylene terephthalate esterification reaction. The bottoms from column F consists of about 10 percent water and 90 percent ethylene glycol and contains about 1.6 to 1.7 percent by weight of solids. If two additional reactor vessels, in addition to A, B and C are included to feed condenser D, the solids content of the recycle ethylene glycol would increase to about 2 percent by weight. The temperature at the bottom of the distillation column F is 140° C., at atmospheric pressure, the corresponding temperature at the top of the distillation column F is 100° C. The distillation column F has 14 distillation plates. The temperature in the column drops to about 100° C. (±1° C.) by the tenth tray. This shows that a distillation column of 10 or more trays could be used in this process. The principal byproduct impurities in the bottom being recycled to ethylene glycol storage tank E are diisopropylamine, diethylene glycol oligomers, and traces of polyaldehydes. Diisopropylamine is an additive used in reactors A, B and C to suppress the formation of diethylene glycol in the polyethylene terephthalate polymers. Other impurities may be present. See U.S. Pat. No. 3,367,847, hereby incorporated by reference in toto. The feed rate of the condensed vapors through 11 to column F is about 8 to 12 gallons (30 to 45 liters) per minute at a temperature of about 65° C. and is fed to a point just above the third distillation plate in distillation column F. The spray condenser for the overhead from column F circulates 296 gallons (1120 liters) per minute of water from a cooling tower to condense 2600 to 3800 pounds (1180 to 1727 kg) per hour of water vapor and what few impurities come overhead. The bottoms is recirculated to the reboiler at a rate of 1000 gallons (3785 liters) per minute. Steam is fed to the reboiler at 3500 pounds (1590 kg) per hour at 110 psig (7.7 kg/cm$^2$) when the reboiler tubes are clean but tube pressure may have to increase to about 145 psig (10.2 kg/cm$^2$) as the tubes in the reboiler become dirty. Ethylene glycol is recovered from the bottoms and pumped to storage tank H at a rate of about 4 gallons (15 liters) per minute at a temperature of about 140° C. Also bottoms is recirculated at a rate of 75 gallons (284 liters) per minute through the cooler J so that the final exit temperature can be brought down to 45° C. It is highly preferable to use a silicone antifoam by adding it to the storage tank H or to the recycle ethylene glycol 21 to storage. This antifoam is necessary to keep down foaming in reactor vessels A, B, C or any others that may be present in other processing. This provides about 5 to 10 percent higher capacity in the reactor vessels A, B and C not previously available prior to this recycle system. Recycle also provides a much higher raw material yield because the ethylene glycol is recycled but yet with no apparent deficiency and a surprising benefit in the lower diethylene glycol content, 1.2 wt. percent as compared to virgin ethylene glycol feed polymer of 1.3 wt. percent, of the final polyethylene terephthalate polymer being manufactured in reactors A, B, and c. This is surprising since only part of the water and high boilers are removed from the recovered ethylene glycol. There is no noticeable effect on yarn quality, production yields, polymer color or yarn color.

We claim:

1. A method to recycle spent ethylene glycol in a continuous process for the manufacture of polyethylene terephthalate in at least one reactor vessel, said method consisting essentially of:
   a. condensing overhead vapor of spent ethylene glycol, water and other byproducts comprising diisopropylamine, diethylene glycol oligomers, and trace amount of polyaldehydes from the reactor vessel,
   b. feeding said condensed vapor to a single distillation column,
   c. removing only part of the water and said other byproducts from ethylene glycol by distillation overhead in said column, and
   d. feeding a portion of the resultant bottoms of said column back to the reactor vessel directly as recycle ethylene glycol along with virgin ethylene glycol, said recycle ethylene glycol containing at least about 1 but less than about 3 percent by weight of solids and containing byproducts comprising diisopropylamine, diethylene glycol oligomers, and trace amounts of polyaldehydes,
   so that polyethylene terephthalate polymer being manufactured by said continuous process is substantially unaffected regarding polymer color and ability to be spun into yarn, but with lower diethylene glycol content than polymer produced from all virgin ethylene glycol;
   wherein the feed to said distillation column contains from about 45 to about 55 percent ethylene glycol, the overhead from said distillation column contains from about 0.1 to 1 percent ethylene glycol, and the bottoms of said distillation column to be recycled contain from about 85 to about 95 percent ethylene glycol;
   wherein said bottoms from said distillation column is recirculated through a reboiler for heating to achieve a bottom temperature of from between about 130° and 150° C.; and
   wherein an antifoaming compound is added to a recycle system.

2. The method of claim 1 wherein said distillation column also has a reflux of 100 percent clarified water.

3. The method of claim 2 wherein the reflux ratio is from about 0.12 to 1.0.

4. The method of claim 1 wherein the temperature at the top of said distillation column is from about 100° C. to about 105° C.

5. The method of claim 4 wherein said column has from about 10 to about 16 distillation plates.

6. The method of claim 5 wherein the feed rate to said distillation column is from about 8 to about 12 gallons (30 to about 45 liters) per minute at a temperature of about 65° C. and is fed to a third distillation plate in said column.

7. The method of claim 1 wherein the pressure in the column is between about 400 to 760 Torr.

8. The method of claim 1 wherein between abut 850 and about 1250 gallons (3200 and about 4730 liters) per minute are recirculated through said reboiler, and steam is fed to said reboiler at about 3500 to 4500 pounds (1590 to 2045 kg) per hour at a pressure of between 110 and 145 psig (7.7 and 10.2 kg/cm$^2$).

9. The method of claim 1 wherein a reflux of clarified water at a reflux ratio of from about 0.12 to 1 is refluxed in said distillation column and the temperature at the top of said distillation column is between 100° and 105° C., said distillation column is operated at a pressure of between abut 400 Torr to about 760 Torr, said distillation column has fourteen plates, said feed rate to said distillation column is from about 8 to about 12 gallons (30 to about 45 liters) per minute at about 65° C. to above the third plate in the distillation column, and said bottoms of said distillation column is recirculated to a reboiler at a rate of from about 850 to about 1250 gallons (3200 to about 4730 liters) per minute, and steam is fed to the reboiler at a rate of abut 3500 to 4500 pounds (1590 to 2045 kg) per hour at 110 to 145 psig (7.7 to 10.2 kg/cm$^2$).

10. The method of claim 9 wherein said at least one reactor vessel comprises multiple reactor vessels.

11. The method of claim 1 wherein said at least one reactor vessel comprises multiple reactor vessels.

* * * * *